United States Patent [19]

Thomas

[11] 4,180,790
[45] Dec. 25, 1979

[54] DYNAMIC ARRAY APERTURE AND FOCUS CONTROL FOR ULTRASONIC IMAGING SYSTEMS

[75] Inventor: Charles E. Thomas, Scotia, N.Y.

[73] Assignee: General Electric Company, Schenectady, N.Y.

[21] Appl. No.: 864,597

[22] Filed: Dec. 27, 1977

[51] Int. Cl.² ............................................. G01S 9/66
[52] U.S. Cl. ...................................... 367/7; 73/626; 367/105
[58] Field of Search .................... 340/1 R, 9; 73/626, 73/629

[56] References Cited

U.S. PATENT DOCUMENTS

| | | | |
|---|---|---|---|
| 3,911,730 | 10/1975 | Niklas | 73/626 |
| 3,936,791 | 2/1976 | Kossoff | 340/1 R |
| 4,012,952 | 3/1977 | Dory | 340/1 R X |
| 4,058,003 | 11/1977 | Macovski | 340/1 R X |

OTHER PUBLICATIONS

Thurston et al., *Acoustical Holography*, vol. 5, 1974, Plenum Press, N. Y., pp. 249-259.

*Primary Examiner*—Richard A. Farley
*Attorney, Agent, or Firm*—Donald R. Campbell; Joseph T. Cohen; Marvin Snyder

[57] ABSTRACT

A B-scan ultrasonic imager such as a single-sector scanner has a dynamic aperture and focus control to attain improved lateral resolution especially at ranges less than the maximum array aperture. As the range from which echoes are being received propagates out, the array aperture during each echo reception period is increased by steps by switching in more elements of the total transducer array. At least one adjustment of receiving channel time delays is made to dynamically focus the echoes at different focal points.

6 Claims, 4 Drawing Figures

STEERING DELAYS

FOCUSING DELAYS

FOCUSED ECHO SIGNAL

DYNAMIC ARRAY APERTURE AND FOCUS CONTROL FOR ULTRASONIC IMAGING SYSTEMS

BACKGROUND OF THE INVENTION

This invention relates to a method and apparatus for ultrasonic imaging, and more particularly to a dynamic electronically controlled aperture in combination with dynamic focusing for improved lateral resolution in sector scanners and other B-scan ultrasonic imaging systems.

One of the most important parameters determining ultrasonic image quality is that of lateral resolution, which refers to a minimum separation at which two targets can be distinguished in the direction of the longitudinal axis of the linear transducer array. Under far field conditions lateral resolution improves as the transducer array aperture increases, whereas under near field conditions lateral resolution improves as the transducer array aperture decreases. It is known that focusing can theoretically establish far field conditions in the near field, so that large aperture would be an advantage at all ranges. However, it is difficult to maintain focus at ranges less than the array aperture even with electronic dynamic focus. In B-scan tomographic cardiac imaging, ranges less than the array aperture are often of interest. Thus, there are important applications where the optimum aperture varies with depth across the image field.

The single-sector scanner is a real time imaging system having a linear transducer array as depicted in FIG. 1, and is described as a cardiac scanner by Thurstone and von Ramm in "A New Ultrasonic Imaging Technique Employing Two-Dimensional Electronic Beam Steering," *Acoustical Holography*, Vol. 5, 1974, Plenum Press, New York, pp. 249-259. To make a sector scan, the elemental transducers are excited in linear time sequence to generate angulated acoustic beams at many angles relative to the normal to the array at its midpoint. Echoes returning from targets in the direction of the transmitted acoustic beam arrive at the transducer elements at different times necessitating relative delaying of the received echo electrical signals by different amounts so that all the signals from a given point target are summed simultaneously by all elements of the array. In addition to beam steering delays, dynamic electronic focusing to improve image quality is achieved by additional channel-to-channel delay differences to compensate for propagation path time delay differences from a focal point to the various individual array element positions. The beam steering and electronic focusing delays are additive, and the focus can be changed dynamically to increment the range from which echoes are being received during a reception period. In the prior art sector scanners the entire array of receive elements are active during an echo reception period and the received signals from all receive elements are delayed and summed to generate a focused echo signal or video signal. That is, the array aperture during each echo reception period is unchanged and is the maximum possible aperture. At ranges less than the maximum aperture, dynamic focusing delays must be changed so rapidly that it becomes nearly impossible to keep up.

SUMMARY OF THE INVENTION

To achieve improved lateral resolution in an ultrasonic imaging system with a linear array of transducer elements, especially at ranges less than the full array aperture, the array aperture is increased as the range from which echoes are being received increases by effectively switching in more array elements by steps during every echo reception period. The dynamic aperture control for best image quality is combined with a dynamic focus control for adjusting time delays in the echo signal processing channels to focus the echoes at a plurality of focal points at different ranges. At longer ranges, several times the full array aperture, all of the array elements and echo processing channels are switched in or are active for the best realizable lateral resolution.

The exemplary embodiment is an improved signal sector scanner for real time medical imaging in which there is a switch, or equivalent mechanism for blanking receiving channels individually, between every array element and associated receiving channel. Initially, only the central group of elements and receiving channels are active during the echo reception period, and as the range increases the elements and receiving channels are switched on symmetrically by two's, one at either side, until all the elements are active and the maximum aperture is attained. Changes in aperture size are made during the interval the range is less than the maximum aperture until the range is several times the maximum aperture, and at least one adjustment of focusing time delays in the receiving channels is made, the steering time delays remaining the same. The delayed echo signals from the varying number of active receiving channels are summed to generate the focused echo signal or raw video signal which is displayed as a visual image of the insonified object region on a cathode ray tube monitor. The dynamic aperture and focus control is also applicable to the multi-sector scanner and digital rectilinear scanner, both of which are described in identified copending patent applications.

DESCRIPTION OF THE PREFERRED EMBODIMENTS

The system for dynamic control of array aperture during every echo reception period of a B-scan ultrasonic imaging system can theoretically be used with any imaging system that has an array of transducer elements for echo reception, whether that system employs no focusing, mechanical focusing, fixed electronic focusing, or dynamic electronic focusing. There are certain advantages, however, in the combination of a dynamic array aperture control with a dynamic focusing control in medical instrumentation for cardiology and laminography, where good images with improved lateral resolution in the near field region are needed, and in ultrasonic imagers for similar industrial applications. The dynamic array aperture and focus control can be used with both rectilinear and sector scan systems, and with systems that have or do not have array apodization. The preferred embodiment is a single-sector scanner for imaging the beating heart in real time.

Figure 1:
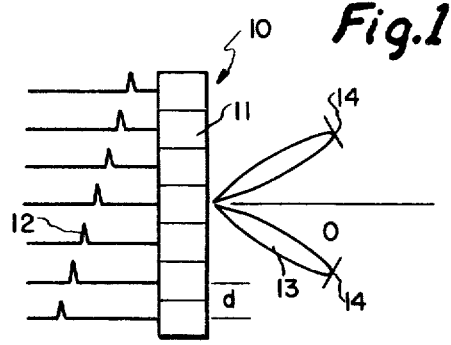
FIG. 1 is a sketch illustrating operation of a single-sector steered beam ultrasonic imager.

The single sector steered beam ultrasonic scanner in FIG. 1 has a linear transducer array 10 comprising equally spaced elementary transducers 11 which are energized by excitation pulses 12 in a linear time sequence to form an ultrasound beam 13 and direct the beam in a preselected azimuth direction to transmit a pulse of ultrasound. The linear transducer array is also referred to as the phased array. In order to steer the beam electronically to an angle $\theta$ degrees from the normal to the array longitudinal axis, a time delay increment $$T_i = (i-1)d \sin \theta / c \qquad (1)$$

where c is the sonic velocity, is added successively to each i th signal as one moves down the array from one end (i=1) to the other (i=N) to exactly compensate for the propagation path time delay differences that exist under plane wave (Fraunhofer) conditions. By progressively changing the time delay between the successive excitation pulses, the angle $\theta$ at one side of the normal is changed by increments. To form and steer the beam at the other side of the normal, the timing of excitation pulses 12 is reversed so that the bottom transducer in FIG. 1 is energized first and the top transducer is energized last. The total sector scan angle is approximately 60° to 90°. Echoes returning from targets 14 in the direction of the transmitted beam arrive at the transducer elements at different times necessitating relative delaying of the received echo electrical signals by different amounts so that all the signals from a given point target are summed simultaneously by all elements of the array. Within the focal region in the near field the acoustic beam actually appears as if it were in the far field as in FIG. 1, and this is further explained in [Electronic Scanning of Focused Arrays] by V. G. Welsby, *Journal of Sound Vibration* (1968), Vol. 8, No. 3, pps. 390-394. The magnitudes of the time delays of the individual echo electrical signals are the same as during the transmission operation to compensate for acoustic path propagation delay differences. These are referred to as the beam steering time delays, or simply steering delays.

In B-scan imaging focusing is not essential but improves image quality by increasing resolution and reducing some kinds of artifact problems. Electronic focusing, like beam steering, is accomplished by the use of channel-to-channel electronic signal delay differences to compensate for propagation path time delay differences from the focal point to the various individual array element positions. The electronic focusing delay increment for each sub-array is given by $$T_k = (a^2/2fc)[1-(x_k/a)^2], \qquad (2)$$

where
- a = the sub-array half aperture distance,
- f = the focal distance,
- c = the sonic velocity,
- $x_k$ = the distance from the sub-array center to the k th element, and
- $T_k$ = the time delay associated with the k th element.

It has been shown that the beam steering and focusing time delays are additive, i.e., if one applies the time delay set required to steer the beam to an angle $\theta$ and then adds the time delay set required to focus at a range R, the focal point will be located at range R measured along an axis $\theta$ degrees from the normal to the longitudinal axis of the sub-array. The receiving focus, unlike the transmitting focus, can be dynamically changed to track the range from which echoes are being received during the echo reception period by a one step or multistep approximation. The additive nature of steering and focusing time delay sets is an approximation that is good except at very short ranges.

Figure 2:
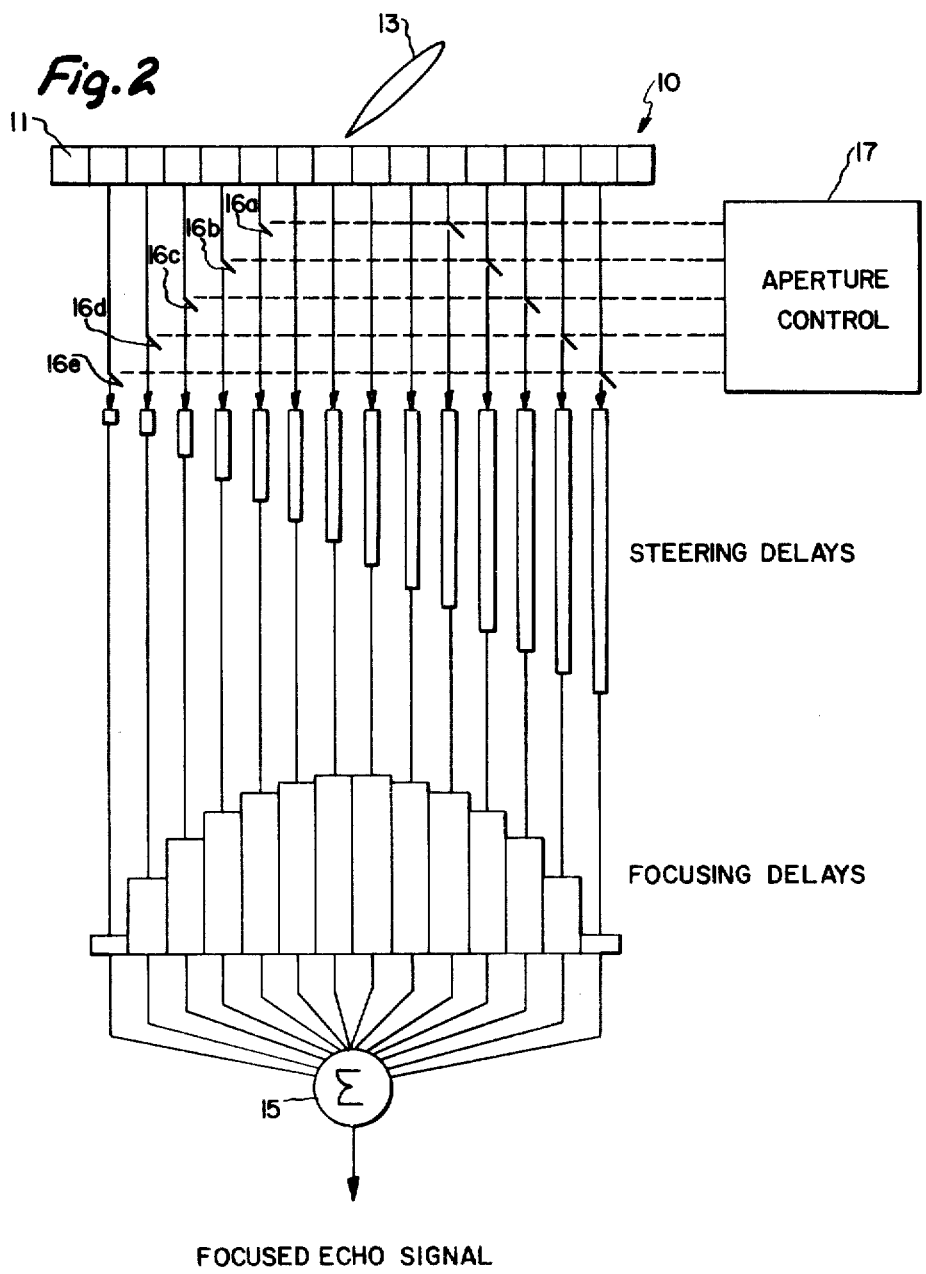
FIG. 2 schematically depicts time delay steering and focusing of received echo signals from a receive array of transducer elements.

In FIG. 2, the steering and focusing time delays are indicated separately in the receiving channels associated with array transducer elements 11, and are depicted as rectangular blocks which vary in length from channel to channel. To effect coherent summation of the contributions from all active receive elements, the delayed echo signals from the multiple receiving channels are fed to a summing amplifier 15 at the output of which is a focused echo signal or raw video data. After being processed through a scan converter to convert the sector scan format to raster format, the focused echo signal controls the electron beam intensity of a cathode ray tube or television monitor as the image is built up scan line by scan line. This is further explained in detail with regard to FIG. 4. The steering time delays remain the same during each echo reception period for a transmitted and steered pulse of ultrasound, and are changed between echo reception periods to correspond to the angulation of the next transmitted acoustic beam. The focusing time delays, on the other hand, are adjusted dynamically during every echo reception period to focus the received echoes at a plurality of focal points as the range propagates out. A typical operation to scan the object for one image frame is that the transducer elements of array 10 are energized in sequence with the delays initially set to generate a transmitted acoustic beam at the farthest possible clockwise position, the received echo signals being delayed in the same order to steer the channel signals with additional relative delays for focusing the echoes. In succeeding transmit-receive cycles, the relative channel-to-channel time delays are progressively changed to rotate the generated acoustic beam by small angular increments in the counterclockwise direction toward the farthest possible counterclockwise position. During each transmit-receive cycle, the additional relative channel delays that control the focal range are dynamically changed so that the focal range tracks the echo-generation region. This monotonic counterclockwise increase of the acoustic beam direction is not essential; the beam steering delays can be controlled to select beam directions in any desired order. A frame rate of about 30 frames per second is needed to prevent blurring of the image of the portion of the heart being pictured on the television screen.

In addition to changing the focusing delays at least once during every echo reception period, improved lateral resolution in the image is attained by dynamically controlling the array aperture as a function of range such that the aperture is increased by steps at ranges less than the maximum array aperture and normally extended up to ranges several times the maximum array aperture. At ranges further out approaching or in the far field, lateral resolution improves as the transducer array aperture increases and there is benefit in using the maximum possible array aperture. Under far field conditions, the reflected echo acoustic wave fronts arriving at the transducer array are plane or approximately plane. Focusing can theoretically establish far field conditions in the near field so that a large aperture would be an advantage at all ranges, but in practice it is difficult to maintain focus at ranges less than the array aperture even with dynamic electronic focusing. Aperture control to improve lateral resolution at short ranges is implemented by structuring the receiver so that the individual channels can be blanked electronically with the possible exception of a central group of receiving channels. The number of active receive elements and receiving channels is then increased symmetrically by steps until the maximum array aperture is reached with all the receive elements and receiving channels active.

The dynamic aperture control is shown schematically in FIG. 2 as pairs of receiver channel switches 16a–16e which are closed in sequence during the echo reception period, one pair at a time, by an aperture control circuit 17. Receiving channel switches 16a–16e operate at high speed and are actually electronic switches, but the function of blanking the channels can be performed in an equivalent manner by reducing the amplifier gain or otherwise. At the shortest ranges, well within the maximum array aperture, only the four central array transducers are connected to their respective receiving channels and the delayed echo signals in only these four channels are summed to generate the focused echo signal. As the range increases, switches 16a, one on either side of the central group of four, are closed, and then pairs of switches 16b–16e are closed in sequence, thereby incrementally increasing the size of the receiver sub-array and the number of active receiving channels whose delayed echo signals are summed by summing amplifier 15. As a rule of thumb in the near field, beam width is approximately equal to the size of the aperture, and lateral resolution varies with the size of the aperture and therefore is best when the aperture is small.

Figure 3:
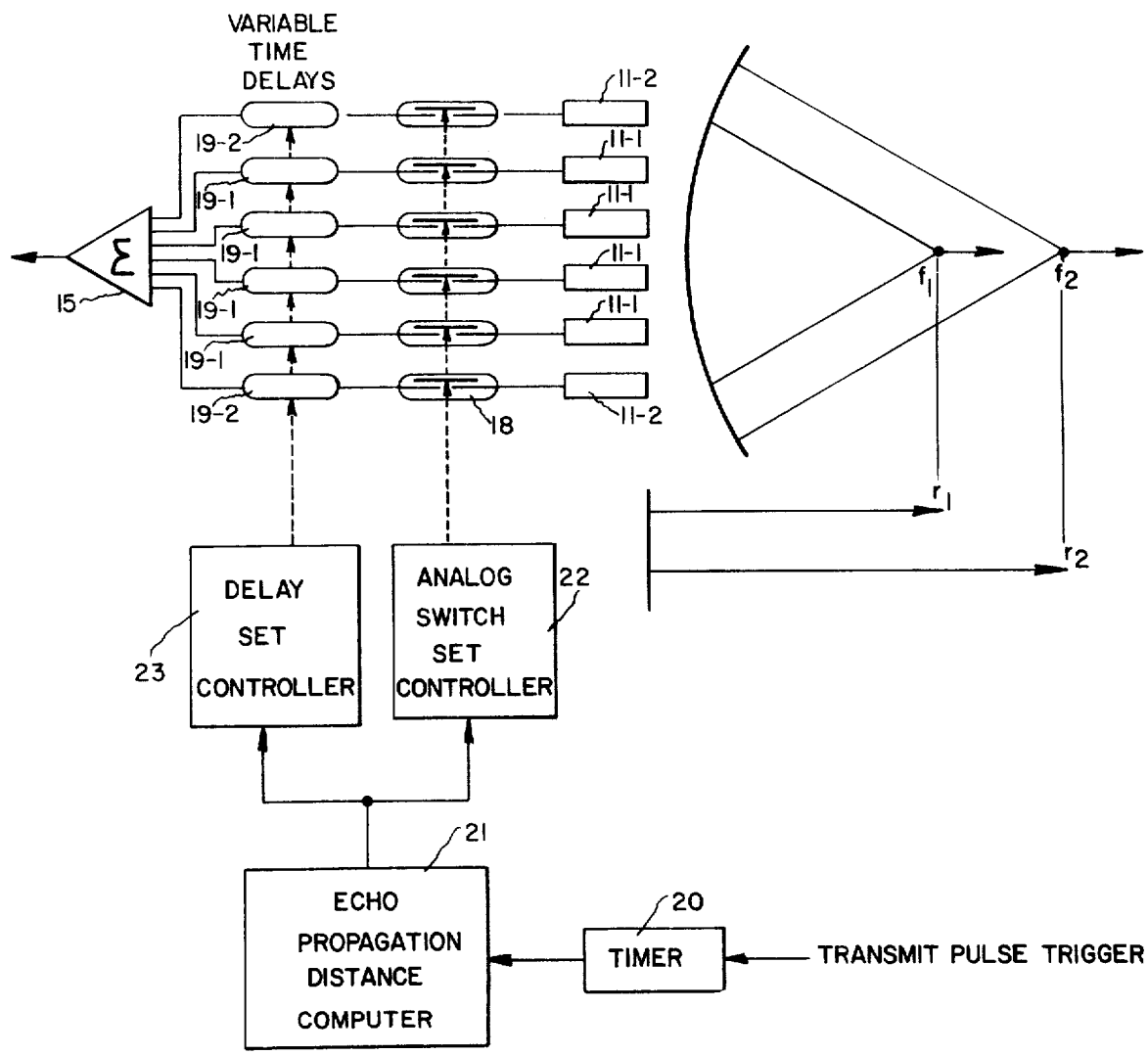
FIG. 3 shows a simplified receiving channel diagram for a system with dynamic aperture and focus control.

For cardiac scanning, linear transducer arrays can typically have a length of 40 millimeters or 4 centimeters, and the width of the elementary transducer is between 0.5 and 1.0 millimeter. There can be more receive elements than transmit elements, and they need not be equally spaced. For these dimensions, the maximum array aperture is 4 centimeters and it is seen that details of a heart being examined at ranges of less than 4 centimeters are often of interest. The maximum range can be 25 centimeters, and it is desirable to have the aperture control up to about one-half the maximum range or 12 centimeters. This is three times the full aperture. The frequency with which changes in the focusing time delays to vary the focal length must be made, consistent with the objective of good picture quality, also decreases as the range is increased. The dynamic aperture and focus control is illustrated in more general form in FIG. 3 with the addition of details of the aperture control circuit. This system has an analog switch 18 and a variable time delay device 19-1 or 19-2 such as selectable-delay delay line in each array element receiving channel. The steering and focusing delays for a single sector steered beam scanner can be combined in the same device, as for instance a charge coupled device (CCD) delay line comprised of two or more subdelay lines whose delay times are separately controlled. The transmit pulse trigger starts a timer 20 whose function is to blank out the array transducer elements for a brief interval at ranges very close to the array to allow reverberations to decay. At the end of a preset interval an echo propagation distance computer 21 begins to calculate the range and required time delays based on the elapsed time for two-way propagation of sound and the velocity of sound in tissue, about 154,000 centimeters per second. Computer outputs generated at predetermined ranges control both an analog switch set controller 22 and a delay set controller 23. As the range from which echoes are being received propagates out, the array aperture is increased in steps by switching in more elements of the total transducer array. Shortly after pulsing the central group of transducers 11-1, the associated analog switches 18 are closed to connect the elements to the receiving channels and the delays of devices 19-1 are adjusted for a focus at $f_1$ and the echoes are coming from range $r_1$. When propagation distance computer 21 indicates that echoes are being received from range $r_2$, elements 11-2 and delay devices 19-2 are connected in the receiver circuit with the delays adjusted to provide a focus at $f_2$. If array apodization is used, it is desirable to adjust element weights when the aperture is adjusted. For the case where there are more elements in the total transducer array, the aperture is increased symmetrically in steps of two. A central group of transducers is ordinarily either two or four elements.

Figure 4:
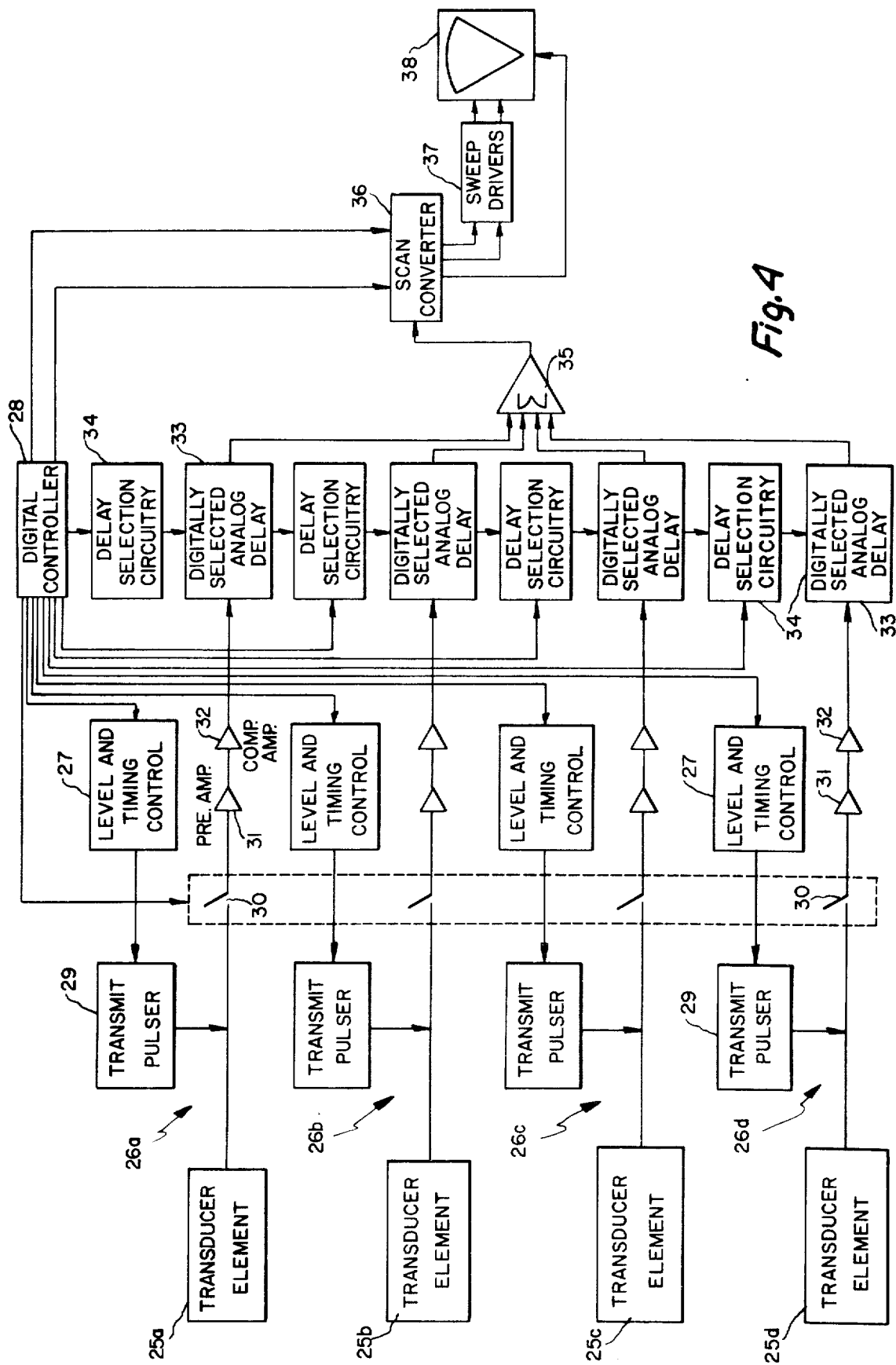
FIG. 4 is a functional block diagram of a single-sector scanner imaging system incorporating the dynamic aperture and focus control.

FIG. 4 is a system block diagram of the single sector scanner ultrasonic imager with provision for dynamic aperture and focus control at short ranges in the near field for improved lateral resolution. The linear transducer array is illustrated with only four transducer elements 25a–25d, but in practice the array has a larger number of elements, some of which may be receive only elements. The four transmitting and receiving channels 26a–26d are each comprised by level and timing control circuitry 27 under the control of a master digital controller 28 for determining the level and timing of a pulse generated by transmit pulser 29 and applied to one of the transducer elements. The receiving channel for processing the received echo electrical signal is comprised by an analog switch 30, a preamplifier 31 having a limiter to protect the sensitive preamplifier inputs from the high transmitting voltage, and a compression amplifier 32 to reduce the larger dynamic acoustic range to the smaller range a cathode ray tube display device can handle. The amplified echo signal is next fed to a digitally selected analog delay device 33 having associated delay selection circuitry 34 which, under the control of digital controller 28, presets the delay to steer and focus the echo signal in that channel. The other three receiving channels are identical except for the values of the time delays employed. Digital controller 28 can take various forms and can be a hard wired logic circuit but is preferably a properly programmed microcomputer or minicomputer incorporating the functions of the aperture control (timer, echo distance computer, and controllers) in FIG. 3. In operation, transducer excitation pulses are generated in the four transmitting channels in time sequence to steer the generated ultrasound beam and control the scan angle. During the echo reception period, the central two analog switches 30 are closed, after a short interval to reject reverberations, and the received echo signals generated by elements 25b and 25c are delayed by different preset amounts to steer and focus the echoes at a first focal point. At a predetermined range, the two outer switches are closed to increase the array aperture by switching in elements 25a and 25d, and the focusing time delays are adjusted to focus the echoes at a second focal point. The delayed echo signals from all active receiving channels, either two or four, are fed to a summing amplifier 35 to generate the focused echo signal which is presented to a scan converter 36 before being displayed. The scan converter is described in copending application Ser. No. 853,347, filed on Nov. 21, 1977 by J. J. Tiemann, entitled "Scan Converter For Ultrasonic Sector Scanner" and assigned to the same assignee as this invention. Other types of scan converters such as an analog storage tube can also be used. The scan converter controls sweep drivers 37 and the generated X and Y deflection signals for cathode ray tube 38 on the screen of which is displayed, in real time, the single sector image. During every succeeding echo reception period following generation of an acoustic beam at a different scan angle, the array aperture is dynamically increased in combination with adjusting the focusing time delays and focal point.

The dynamic aperture and focus control can be employed in other ultrasonic imaging systems with a linear array of transducer elements. It is applicable to imaging systems that do not use scan converters, but instead cause the movement of the beam of the cathode ray tube to directly follow the movement of the acoustic echo region in the propagating medium in real time. It is directly applicable without further explanation to the multi-sector scanner disclosed in allowed copending application Ser. No. 825,528, filed on Aug. 18, 1977 by H. A. F. Rocha jointly with the present inventor. This system has a longer linear transducer array for producing a set of sector scans with the origin points of the sequential sector scans displaced longitudinally along the array. A digital rectilinear ultrasonic imaging system is described in U.S. Pat. No. 4,127,034 granted on Nov. 28, 1978 to F. L. Lederman and J. J. Tiemann. This new architecture has a linear transducer array wherein the elements are pulsed one at a time while alternately storing the received echo signals in a long, segmented digital delay line memory having a number of delay lines equal to the number of elements in a receive sub-array. After N pulses, the N transducers in the array have been selected, and their outputs are simultaneously present at the N taps of the segmented delay line. Upon shifting the receive element echo data from one delay line to the next, the echo data read out of all delay lines are also processed through parallel channels where the data is subjected to focusing delays and then fed to a summing amplifier for coherent summation. In this case, an array aperture control is effected by blanking out processing channels before coherent summation so that the number of channels fed to the summing amplifier and the number of receive elements contributing to the focused echo signal increased by steps as a function of range. Both of the foregoing applications are assigned to the same assignee as this invention.

To summarize, the method of ultrasonic imaging for improved lateral resolution and picture quality comprises processing the echo signals from separate receive elements in parallel channels for delaying the echo signals by variable amounts in the different channels to focus the received echoes; changing the number of contributing active signal processing channels and therefore the number of effectively active receive elements as a function of range during the echo reception period to increase the array aperture by steps; adjusting the processing channel time delays at least once during the echo reception period to dynamically focus the echoes; and continuously summing the delayed echo signals from all active signal processing channels.

The components of an ultrasonic scanner with the dynamic aperture and focus control can be standard integrated circuits or conventional circuitry as is presently known in the art. Further information on sector scanners for real time imaging is given in the previously referenced publications and patent applications.

While the invention has been particularly known and described with reference to preferred embodiments thereof, it will be understood by those skilled in the art that various changes in form and details may be made therein without departing from the spirit and scope of the invention.

The invention claimed is:

1. An ultrasonic imaging system with improved lateral resolution comprising:
   a linear array of transducer elements which are selectively operative during alternate transmission and echo reception periods to sequentially generate pulses of ultrasound for scanning an object region and to generate received echo electrical signals,
   a plurality of transmitting channels for producing excitation pulses for selected array elements, and a plurality of receiving channels connected to the array elements for delaying the echo signals for variable predetermined time delays to focus the received echoes,
   aperture control means for increasing the number of active array elements and receiving channels as a function of range during each echo reception period such that a central group of receiving channels are initially active and thereafter pairs of receiving channels, one on either side, are additionally rendered active whereby the array aperture is increased by steps at least during the interval the range does not exceed the maximum aperture,
   means for adjusting the receiving channel time delays at least once during each echo reception period to dynamically focus the received echoes at a plurality of focal points at different ranges, and
   means for summing the delayed echo signals from all active receiving channels to thereby generate a focused echo signal.

2. The imaging system of claim 1 wherein said pairs of receiving channels are rendered active as a function of range during the interval the range is less than the maximum array aperture until the range is several times the maximum array aperture.

3. A single-sector scanner ultrasonic imaging system with improved lateral resolution comprising:
   a linear array of transducer elements which are selectively operative during alternate transmission and echo reception periods to sequentially generate angulated acoustic beams steered at many angles for scanning an object region and to generate received echo electrical signals,
   a plurality of transmitting channels for producing excitation pulses in time sequence for selected array elements, and a plurality of receiving channels connected to the array elements for amplifying and delaying the echo signals for predetermined steering and focusing time delays to focus the received echoes,
   aperture control means for symmetrically switching in and increasing the number of active array elements and receiving channels as a function of range during each echo reception period, at least during the interval the range is less than the maximum array aperture, by initially having a central group of active receiving channels and thereafter switching in successive pairs of receiving channels, one on either side, to increase the array aperture by steps until the total number of receiving channels are active, means for adjusting the receiving channel focusing time delays at least once during each echo reception period to dynamically focus the echoes at a plurality of focal points at different ranges, and means for summing the delayed echo signals from all active receiving channels to generate a focused echo signal and for displaying the focused echo signals as a visual image of the insonified object region.

4. The imaging system of claim 3 wherein said aperture control means is operative to switch in the total number of receiving channels at ranges greater than about three times the maximum array aperture.

5. A method of ultrasonic imaging comprising the steps of:

exciting a linear array of transducer elements to sequentially generate pulses of ultrasound for scanning an object region, said transducer elements during subsequent echo reception periods being operable as receive elements and generating received echo electrical signals, processing said echo signals in parallel channels wherein the echo signals are delayed by variable amounts in the different channels to focus the received echoes, changing the number of active signal processing channels and effectively active receive elements as a function of range during each echo reception period by initially having a central group of active receiving channels and thereafter switching in successive pairs of receiving channels, one on either side, such that the array aperture is increased by steps, adjusting the signal processing channel time delays at least once during each echo reception period to dynamically focus the echoes at a plurality of focal points at different ranges, and summing the delayed echo signals from all active signal processing channels to generate a focused echo signal.

6. The method of claim 5 wherein adjustment of the channel time delays to focus the echoes is coincident with a step change in array aperture.

* * * * *